(12) United States Patent
Riccione

(10) Patent No.: US 9,370,380 B2
(45) Date of Patent: Jun. 21, 2016

(54) EXTERNAL BONE FIXATION SYSTEM

(71) Applicant: DNE, LLC, Slatington, PA (US)

(72) Inventor: Nicholas Riccione, Slatington, PA (US)

(73) Assignee: DNE, LLC, Allentown, PA (US)

( * ) Notice: Subject to any disclaimer, the term of this patent is extended or adjusted under 35 U.S.C. 154(b) by 0 days.

(21) Appl. No.: 13/840,526

(22) Filed: Mar. 15, 2013

(65) Prior Publication Data

US 2014/0276815 A1 Sep. 18, 2014

(51) Int. Cl.
*A61B 17/00* (2006.01)
*A61B 17/64* (2006.01)

(52) U.S. Cl.
CPC ......... *A61B 17/6416* (2013.01); *A61B 17/6433* (2013.01); *A61B 17/6466* (2013.01)

(58) Field of Classification Search
CPC .... A61B 17/60; A61B 17/64; A61B 17/6408; A61B 17/6416; A61B 17/6458; A61B 17/6466; A61B 17/66; A61B 17/6441; A61B 17/6475; A61B 17/6483
USPC ...................................................... 606/53–59
See application file for complete search history.

(56) References Cited

U.S. PATENT DOCUMENTS

| | | | | |
|---|---|---|---|---|
| 4,483,334 A | * | 11/1984 | Murray | 606/59 |
| 4,620,533 A | * | 11/1986 | Mears | A61B 17/645 606/54 |
| 4,628,922 A | * | 12/1986 | Dewar | A61B 17/66 606/54 |
| 5,443,464 A | * | 8/1995 | Russell et al. | 606/54 |
| 5,746,741 A | * | 5/1998 | Kraus et al. | 606/54 |
| 6,162,223 A | * | 12/2000 | Orsak | A61B 17/6425 606/59 |
| 6,340,361 B1 | * | 1/2002 | Kraus et al. | 606/59 |
| 6,409,729 B1 | * | 6/2002 | Martinelli | A61B 17/6466 606/59 |
| 7,465,303 B2 | | 12/2008 | Riccione et al. | |
| 7,678,112 B2 | * | 3/2010 | Rezach | 606/60 |
| 8,235,994 B2 | | 8/2012 | Hollawell | |
| 9,084,630 B2 | * | 7/2015 | Mullaney | A61B 17/6466 |
| 2008/0275507 A1 | * | 11/2008 | Triplett et al. | 606/278 |
| 2011/0251614 A1 | | 10/2011 | Piraino | |
| 2012/0209266 A1 | * | 8/2012 | Ottoboni et al. | 606/59 |
| 2014/0025076 A1 | * | 1/2014 | Lee et al. | 606/59 |

* cited by examiner

*Primary Examiner* — Jacqueline Johanas
*Assistant Examiner* — Tessa Matthews
(74) *Attorney, Agent, or Firm* — Dorsey & Whitney LLP

(57) ABSTRACT

An external fixation assembly for bone fusion or separation is disclosed. The assembly includes a fracture fusion tube, with a bracket slidably engaged thereon. The assembly further includes a collet clamp connected to the bracket, with a ball collet rotatably seated within the clamp, the ball collet having an aperture for receiving a bone bin therethrough and perforations for a compression engagement with a bone pin. The assembly uses a single screw for threadably engaging the ball collet, the clamp and the bracket such that the position of the bone pin, ball collet and bracket are all fixed.

6 Claims, 4 Drawing Sheets

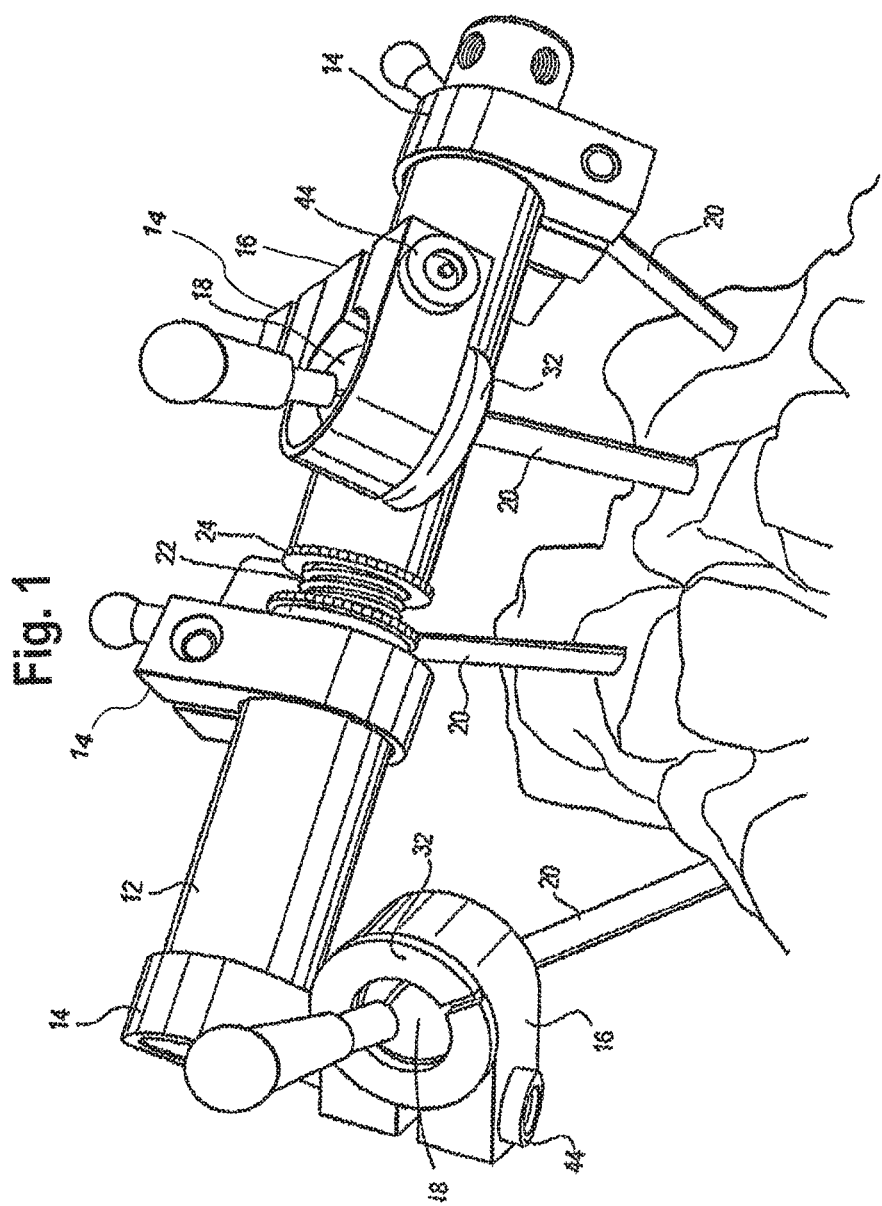

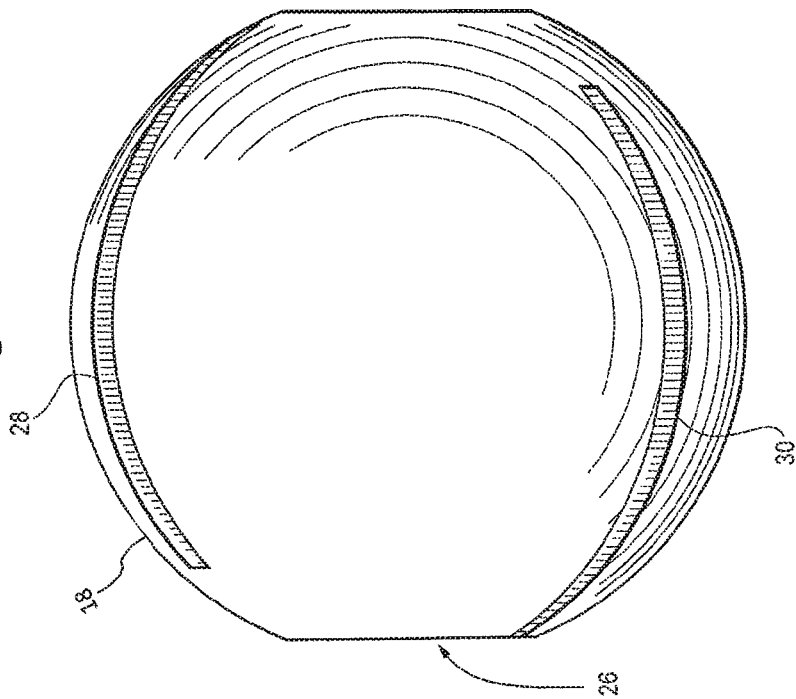
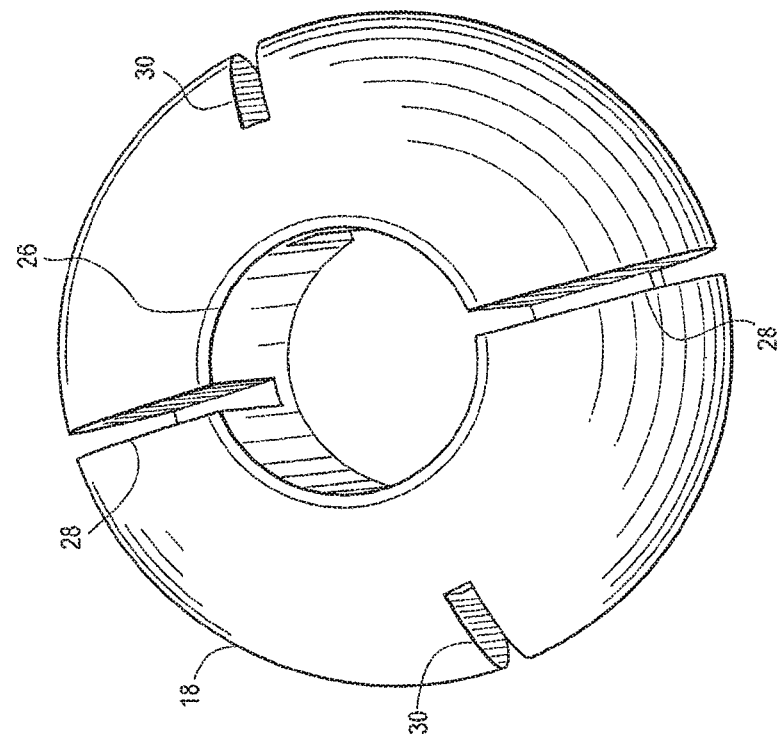

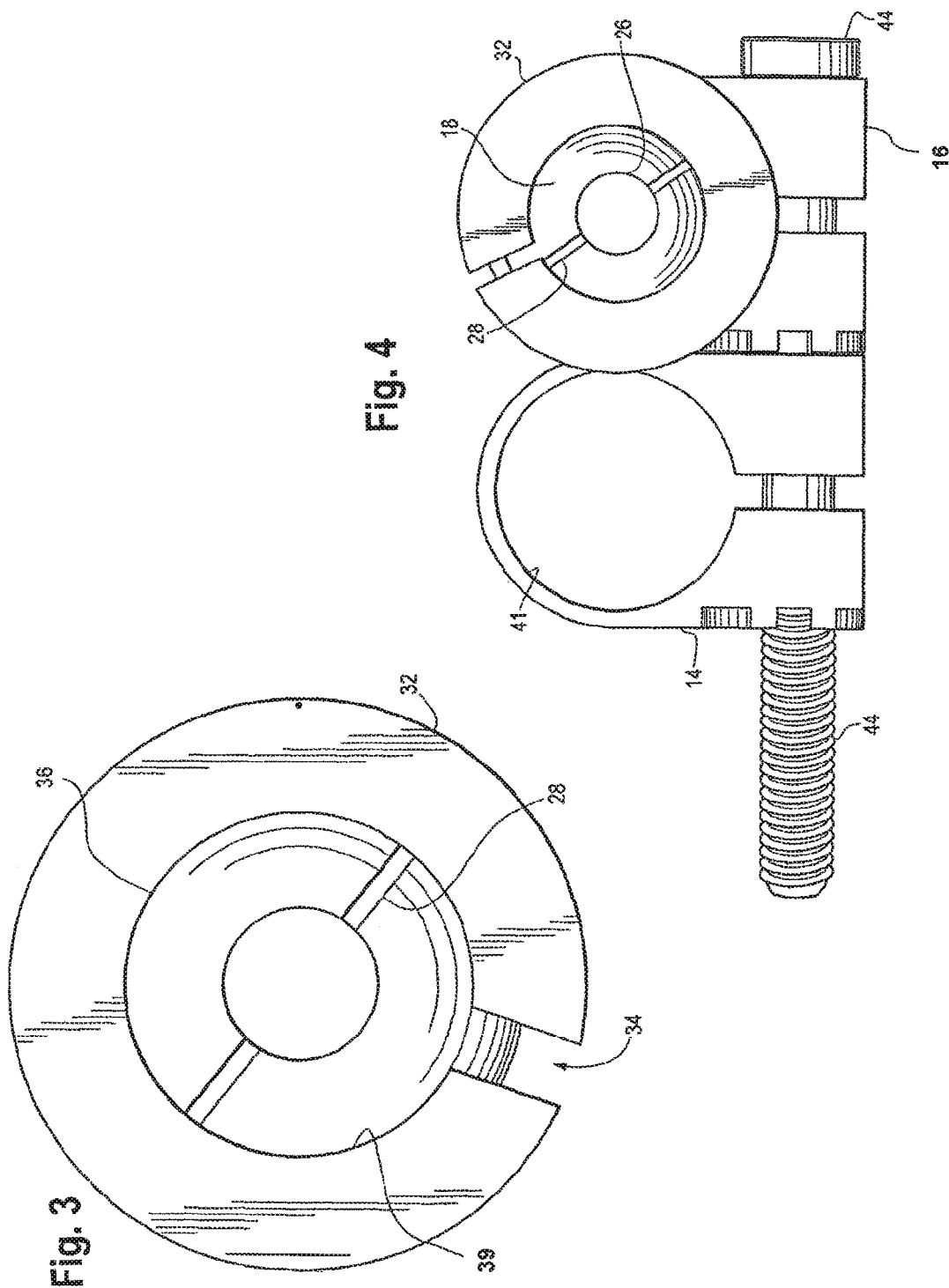

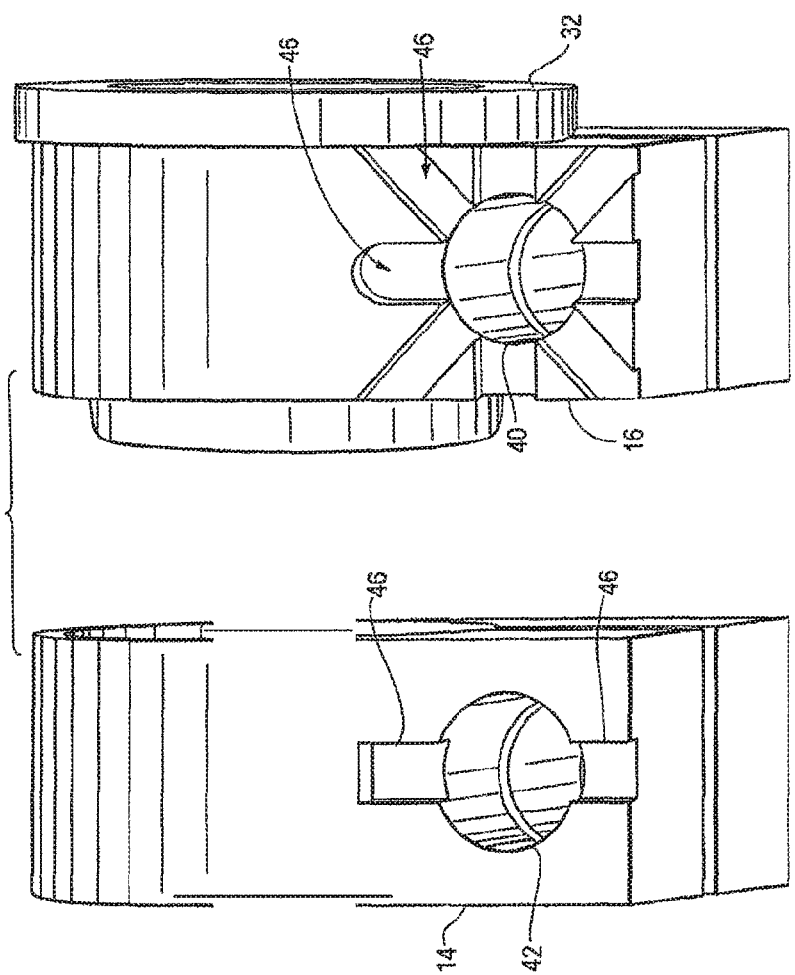

EXTERNAL BONE FIXATION SYSTEM

FIELD OF INVENTION

The present invention relates to an external fixation assembly for bone fusion or separation. More specifically, the assembly includes a fracture fusion tube, with a bracket slidably engaged thereon. The assembly further includes a collet clamp connected to the bracket, with a perforated ball rotatably seated within the clamp, the ball having an aperture for receiving a bone bin therethrough. The assembly uses a single screw for threadably engaging the pin collet, the clamp and the bracket such that the position of the ball, bracket, and collet clamp is fixed. Thus, the present invention teaches an assembly for external fixation with multiple axes of rotation for pin placement and setting wherein the desired placement may be fixed through the use of a single screw or similar connector.

BACKGROUND OF THE INVENTION

External fixation devices have been commonly used for various treatments of bone conditions. Such bone conditions include leg lengthening, osteotomies, arthrodesis, open fracture fixations, compound fracture fixations, and other bone conditions amenable to treatment by use of an external fixation assembly. For example, external fixation devices are typically used in treatment of bones wherein frequent wound care is necessary to treat an open wound or a surgical site within an extremity.

Although current external fixation devices are adequate, many external fixation devices are relatively large and include numerous components, are complicated to use, difficult to adjust, and involve challenging postoperative care and use. Thus, improvements may be made. For example, current external fixation devices involve relatively large and numerous components, creating operative difficulties to both the practitioner and postoperative difficulties to the patient. Many devices, for instance, involve a ring or "halo" member disposed about an affected area to provide support to pins for fixating bone matter. Such components, however effective, are relatively bulky and create difficulty for the physician to insert the pin and for the patient to move independently.

These ring or halo fixation devices have been used by orthopedic surgeons and podiatrists in the treatment of some foot injuries and maladies. Some injuries or conditions involving the foot or ankle require that these devices be applied to the bones of the foot (e.g., calcaneus, tarsals, metatarsals, and phalanges) and the lower leg bones (e.g., tibia and fibula). In such circumstances, pins may be inserted into both the foot and lower leg bones in order to secure the fixation device. However, assemblies currently available in the art have limited rotational ability for a given pin, which is exacerbated by the complex and varied placement of a set of pins being used in a given assembly.

There is a need to provide an external fixation device that involves less components and may be used to articulate a bone pin around multiple axes of rotation while still being relatively easy to use and secure.

Thus, the present state of the art reflects a need for an improved external fracture pin assembly which has a simpler fastening arrangement and greater rotational and angular bone pin adjustability features.

DESCRIPTION OF THE PRIOR ART

One example of a prior art approach is found in U.S. Pat. No. 7,465,303 (Riccione et al.). Among other embodiments, Riccione teaches the use of a plurality of compression nuts, the threads of which are mateable with the threads of a threaded rod. Riccione et al. further comprises one or more collets comprising collet sleeves and collet nuts. The one or more collets are configured to hold a bone pin and to form a compression lock in the apertures when the collet nuts are tightened against the pin holding elements during use. This patent, however, fails to teach multiple orientational components, such as a slideable bracket, a collet and/or other components which may be fixed in location through the use of a single fastener.

Another discussion of a prior art approach may be found in U.S. Pat. No. 8,235,994 (Hollawell), which teaches a fixator for use in the reconstruction of acute, chronic and traumatic injuries to the upper and lower extremities. Specifically, Hollawell teaches a unique clamping system that allows for the snapping in of pins and rails, and for multi-planar fixation of bones. However, Hollawell fails to teach the ability to independently rotate and setting a pin within a collet clamp having a fixed location, nor does it teach the ability to have multiple independently rotatable axes for fixing a pin location wherein the system may be fixed in location using a single fastener.

What is needed is an external bone pin assembly with increased range of motion and decreased complexity of assembly and use.

DEFINITION OF TERMS

The following terms are used in the claims of the patent as filed and are intended to have their broadest plain and ordinary meaning consistent with the requirements of the law.

A "rod", "pin", and "nail" are used interchangeably. All three terms refer to a rigid elongated component that is inserted into one or more bones for the purpose of anchoring, stabilizing, repairing, or supporting the bone(s). The term "rod" usually implies a relatively large device, while the term "pin" implies a somewhat smaller device; however, there is no clear boundary between these terms. In addition, the term "rod" (and the terms "rail," and "tube," too) is not limited to a cross-sectional shape, and may in fact be circular, oval, square, rectangular, polygonal or any combination thereof, while still falling within the term "rod" as used herein.

As used herein, the term "threaded" indicates that a rod or pin has screw-type threads on its external surface; however, a non-threaded rod or pin can have one or more threaded holes passing through it, for fixation screws, so long as the threads are not exposed on the external surface. A rod externally threaded along at least a part thereof is generally referred to as a screw. The screws maybe threaded at one or both ends of the screws based on the preferred use of the screw. However, it should be noted that in some cases non-threaded rods or pins can be used and would still fall within the scope of a "threaded engagement" as used herein, especially where the non-threaded pin is attached to another element (e.g., bone, plate, rod, pin) sufficiently to hold the rod to the element.

It should also be noted that, while the terms "rod", "pin", or "nail" normally tend to imply that an implant does not have an externally threaded surface, some implanted rods, pins, or nails have external threads. Accordingly, such rods can be provided with one or more externally threaded regions if desired, and would still fall within the term "pin" as used herein.

Where alternative meanings are possible, the broadest meaning is intended. All words used in the claims set forth below are intended to be used in the normal, customary usage of grammar and the English language.

OBJECTS AND SUMMARY OF THE INVENTION

The apparatus and method of the present invention generally includes an external bone pin assembly that includes a fracture fusion tube for slidably engaging one or more bracket (which may be a clamp or similar structure). At least one bracket is connected to a collet clamp or similar structure which is rotatable around the circumference of the fracture fusion tube. The collet clamp has seated therein a perforated ball for receiving a bone pin therethrough, the ball being rotatable within the collet clamp for adjusting the angle of engagement for the bone pin and the bone. The perforated ball is composed of aluminum or a similar crushable material. The collet clamp and the bracket have aligned apertures, at least one of which is threaded, and a single screw can be aligned with both apertures, such that tightening a single screw will secure the bracket and collet clamp into a fixed position, and the compressive force of the collet clamp from the tightening screw on the perforated ball crimps the ball into a fixed position. Thus, a single screw can fix all of the components from a given pin subassembly extending from the fusion fracture tube.

The immediate application of the present invention will be seen in providing an external bone pin assembly for a simpler assembly, which provides greater pin insertion into metatarsals and other bones in the foot, though the present invention could be applied to other bodily regions, including the tibia and other bones, using a larger scale but similar principle of operation.

Thus, one object of the present invention is to provide an external bone pin assembly wherein multiple axes of orientation can be fixed by a single fastener.

A further object of the present invention is to provide an assembly with a collet clamp containing a crushable ball collet support for a bone pin.

Still another object of the present invention is to provide modular bracket and collet clamp system components to provide more flexible methods of manufacture and assembly.

Yet another object of the present invention is to provide a cut or perforated ball collet for a compression engagement with a bone pin.

It should be noted that not every embodiment of the claimed invention will accomplish each of the objects of the invention set forth above. In addition, further objects of the invention will become apparent based the summary of the invention, the detailed description of preferred embodiments, and as illustrated in the accompanying drawings. Such objects, features, and advantages of the present invention will become more apparent in light of the following detailed description of a best mode embodiment thereof, and as illustrated in the accompanying drawings.

BRIEF DESCRIPTION OF THE DRAWINGS

FIG. 1 shows a perspective view of a first preferred embodiment of the present invention in application to a metatarsal application.

FIGS. 2a and 2b shows aperture and side views, respectively, of the ball shaped pin collet of one preferred embodiment of the present invention.

FIG. 3 shows a perspective view of a ball shaped pin collet inserted into a peek plastic sleeve in accord with one embodiment of the present invention.

FIG. 4 shows a front view of a bracket and collet clamp assembly engaged with the single fastener in accord with one preferred embodiment of the present invention.

FIG. 5 shows a side view of a collet clamp body with a rotation support feature in accord with one preferred embodiment of the present invention.

DETAILED DESCRIPTION OF THE INVENTION

Set forth below is a description of what is currently believed to be the preferred embodiment or best examples of the invention claimed. Future and present alternatives and modifications to this preferred embodiment are contemplated. Any alternatives or modifications which make insubstantial changes in function, in purpose, in structure or in result are intended to be covered by the claims in this patent.

As can be seen in FIG. 1, in one embodiment of the present invention the assembly 10 comprises a bone fusion tube or rail 12, at least one bracket 14, at least one collet clamp 16 which has seated therein a ball collet 18, the collet clamp 16 being attached to the bracket 14, and a pin 20 inserted through the ball collet 18. Generally, the clamp system 10 is configured to connect the rail 12 to the pin 20, which is connected to a bone for fixation and stabilization.

The rails 12 may be any size or shape, and persons of skill in the art will recognize that different application require rails 12 of many differing sizes or shapes, all of which are contemplated herein. The rails 12 may, for example, have a circular, oblong, square, rectangular, or other-shaped cross section. Typically, however, the rails 12 have a round or circular cross-section and are sized in a manner suitable for fixation of small bones, such as those of the foot or hand. Most preferably, foot systems practicing the present invention can use a short rail of 2.25 to 2.75 inches in length, or a standard length rail of 3.75 to 4.75 inches in length. The rails 12 may be composed of many materials including, for example, carbon fiber or high density plastic, which allows the rod to be radiolucent. Optionally, the rails 12 may have one or more recesses 22 or detents 24 which limit the axial sliding capability of brackets 14 mounted thereon.

An example of unique ball collet features used in certain embodiments of the present invention is shown in FIGS. 2a and 2b. The ball collet 18 is made of aluminum or a similar crushable material, and includes an aperture 26 for receiving the bone pin 20 therethrough. Those of skill in the art will appreciate that the aperture 26 may be of a preselected size (e.g., 3 mm, 4 mm, 5 mm or 6 mm) to mate with a corresponding diameter pin 20. The ball collet 18 further preferably includes a first pair of perforations 28 or cuts, and a second pair of perforations 30 or cuts. Looking at the collet from the orientation of the aperture 26 as in FIG. 2a, the first pair of perforations 28 are directly above and below the aperture, while the second pair of perforations are to the left and right of the aperture. As can be seen from the side view of the collet in FIG. 2b, each set of perforations extends approximately 90 percent along the length of the collet, with each pair of perforations 28, 30 extending from opposite sides of the collet 18. In other words, at one of the aperture 26, only the first pair of perforations 28 will extend from the aperture through to the periphery of the ball collet 18, while at the other end of the aperture, only the second set of perforations will so extend. Thus, since neither pair of perforations 28, 30 extends along the entire length of the ball collet, the ball collet 18 can maintain its structural integrity. However, the presence of the perforations provides a "crush zone" such that the application of a compressive force (as provided and explained below) provides a friction fit between the ball collet 18 and the pin 20.

As shown in FIG. 3, the ball collet may be supported by a plastic sleeve 32, although those of skill in the art will understand that the function of the plastic sleeve 32 may be provided by a recess or groove integrally molded within the collet clamp 16 itself in alternative preferred embodiments. An advantage of the plastic sleeve 32, however, is that the structure of the collet clamp 16 and bracket 14 are essentially identical, thus allowing a modular, more simple manufacture and assembly. In those embodiments using the plastic sleeve 32, that feature most preferably comprises a peek plastic sleeve which includes a slit 34 and ridges 36, with the slit 34 allowing for easier placement of the ball collet 18 during assembly, and the ridges 36 retaining the ball collet 18 once inserted. The ball collet 18, though, still has the ability to rotate within the plastic sleeve 32 after placement and before being secured by a fastener (explained in greater detail below) such that the surgeon is afforded a high degree of rotation of the pin 20 and ball collet 18 within the sleeve 32.

As shown in FIG. 4, once the ball collet 18 is inserted in the plastic sleeve 32, those components can be seated within the throughbore 39 of collet clamp 16 and mated with the bracket 14. The collet clamp 16 has a collet clamp support aperture 40 (FIG. 5) extending through the flat bottom of that component. Likewise, the bracket 14 (which in a first preferred embodiment has the same structure as the collet clamp 16) has a bracket throughbore 41 (which slidably engages the rail 12) and bracket support aperture 42. Thus, when the collet clamp support aperture 40 and the bracket support aperture 42 are aligned with one another as shown in FIG. 4, a single screw 44 can connect the bracket 14 to the collet clamp 16, allowing the collet clamp 16 to rotate with the bracket 14 around the circumference of the rail 12. In a variant of this preferred embodiment (as shown in FIG. 5) the bracket 14 and collet clamp 16 can further include support markings 46 or machined faces on the sides of the bracket 14 and collet clamp 16, thus permitting the collet clamp 16 to be rotated relative to the bracket 14 around an axis defined by the collet clamp support aperture 40 and the bracket support aperture.

In one preferred embodiment, only the bracket support aperture 42 is threaded to make threading the screw through the collet clamp 16 and the bracket 14 easier, although both the bracket 14 and the collet clamp 16 may be threaded in alternative embodiments to provide truly identical structures for modular manufacture and assembly. Given the U shaped structures of the bracket 14 and the collet clamp 16, tightening the screw 44 squeezes and provides a friction fit for the bracket 14 around the rail 12, and prevents further movement of the bracket 14 along the length of the rail 12. Likewise, that same tightening action squeezes the bracket 14 and collet clamp 16 together, thus preventing further rotation of the two components relative to one another. Further, the squeezing action also squeezes the U shaped the bracket clamp, which in turn squeezes the sleeve 32 and the ball collet 18 and prevents the further rotation of the ball collet. Ultimately, the tightening action crimps or collapses the perforations 28, 30, which in turn fixes the pin 20 in the collet ball 18. Thus the tightening of a single screw 44 secures each of the different axes of rotation in the assembly 10.

The above description is not intended to limit the meaning of the words used in the following claims that define the invention. Rather, it is contemplated that future modifications in structure, function or result will exist that are not substantial changes and that all such insubstantial changes in what is claimed are intended to be covered by the claims. For instance, certain embodiments of the present invention may not include structures for all of the axes of rotation provided in the most preferred embodiments. One alternative embodiment of the present invention could conceivably use a single fastener 44 without employing the collet ball 18 of the most preferred embodiments, or vice versa. Likewise, it will be appreciated by those skilled in the art that various changes, additions, omissions, and modifications can be made to the illustrated embodiments without departing from the spirit of the present invention. All such modifications and changes are intended to be covered by the following claims.

I claim:

1. An external bone fixation system for attaching to multiple bone pins, the system comprising:
    a fracture fusion tube having at least one of a recess or a detent disposed along a length of the fracture fusion tube; and
    multiple bracket/clamp assemblies removably attached to the fracture fusion tube, wherein each of the bracket/clamp assemblies comprises:
        a bracket slideably attached to the fracture fusion tube, the bracket having a structure that includes a threaded bracket support aperture and a bracket throughbore;
        a pin collet clamp fixed to, and independently rotatable relative to, the bracket, the pin collet clamp including a threaded clamp support aperture and a clamp throughbore;
        a sleeve disposed in the clamp throughbore;
        a ball collet rotatably disposed within the sleeve, and defining an aperture for receiving one of the multiple bone pins therethrough, the direction of the aperture being independently adjustable across multiple planes relative to the bracket and the pin collet clamp; and
        a single screw for threadably engaging the pin collet clamp and the bracket via the clamp support aperture and the bracket support aperture
    wherein tightening the single screw within the clamp support aperture and the bracket support aperture simultaneously tightens the bracket in its attachment to the fracture fusion tube, tightens the bracket and clamp together so that they cannot rotate relative to one another, and compresses the clamp throughbore, which thus crushes the ball collet, thus preventing the ball collet from rotating within the sleeve and tightening an attachment of the aperture of the ball collet over the one bone pin, and
    wherein the at least one recess or detent is disposed along the fracture fusion tube between at least two of the multiple bracket/clamp assemblies, and wherein the at least one recess or detent prevents the bracket/clamp assemblies from sliding past the at least one recess or detent along the fracture fusion tube.

2. The system of claim 1, wherein the sleeve comprises a separate piece inserted into the clamp throughbore of the pin collet clamp.

3. The system of claim 1, wherein the pin collet clamp comprises a first surface feature on a side of the pin collet clamp, and wherein the bracket comprises a second surface feature on a side of the bracket, wherein the first surface feature and the second feature are configured to mate with one another when the side of the pin collet clamp and the side of the bracket are brought together by tightening the single screw.

4. The system of claim 1, wherein the fracture fusion tube is cylindrical.

5. The system of claim 1, wherein the fraction fusion tube has a constant outside diameter, except at the at least one recess or detent.

6. The system of claim 1, wherein the ball collet comprises:
a first pair of cuts extending from a first opening of the ball collet aperture over an outer surface of the ball collet toward a second opening of the ball collet aperture; and
a second pair of cuts extending from the second opening of the ball collet aperture over the outer surface of the ball collet toward the first opening of the ball collet aperture,
wherein each of the first and second pairs of cuts extends along approximately 90 percent of a length of the outer surface, and
wherein the cuts are configured to allow the ball collet to collapse when squeezed within the clamp throughbore of the pin collet clamp.

* * * * *